United States Patent [19]

Smith-Lewis

[11] Patent Number: 4,803,159

[45] Date of Patent: Feb. 7, 1989

[54] ANALYTICAL ELEMENT AND METHOD FOR DETERMINATION OF TOTAL LACATE DEHYDROGENASE

[75] Inventor: Margaret J. Smith-Lewis, Pittsford, N.Y.

[73] Assignee: Eastman Kodak Company, Rochester, N.Y.

[21] Appl. No.: 848,613

[22] Filed: Apr. 7, 1986

Related U.S. Application Data

[63] Continuation-in-part of Ser. No. 740,163, Jun. 3, 1985, abandoned.

[51] Int. Cl.$^4$ ................. C12Q 1/26; G01N 21/77; G01N 1/00; G01N 21/00
[52] U.S. Cl. ......................................... 435/26; 435/805; 436/169; 436/170; 436/175; 436/810; 422/55; 422/56; 422/57; 422/58
[58] Field of Search .................... 435/26, 805; 422/55, 422/56, 57, 58, 59; 436/169, 170, 175, 810

[56] References Cited

U.S. PATENT DOCUMENTS

| | | | |
|---|---|---|---|
| 3,867,258 | 2/1975 | Forgione | 195/99 |
| 3,992,158 | 11/1976 | Przybylowicz et al. | 23/253 TP |
| 4,089,804 | 5/1978 | Falk | 252/356 |
| 4,250,255 | 2/1981 | Sanford | 435/15 |
| 4,258,001 | 3/1981 | Pierce et al. | 422/56 |

FOREIGN PATENT DOCUMENTS 8400779  3/1984  World Int. Prop. O. .

*Primary Examiner*—Robert J. Warden
*Assistant Examiner*—Carol A. Spiegel
*Attorney, Agent, or Firm*—J. Lanny Tucker

[57] ABSTRACT

A multilayer analytical element exhibits improved precision in the assay of total lactate dehydrogenase (LDH). The element also provides reduced susceptibility to total protein and hemoglobin interferences in the assay. The element contains a porous spreading layer composed of a particulate structure. A fluorinated surfactant is also used in the assay. This surfactant has one or more fluorocarbon moieties provided, that when the surfactant has more than one such moiety, they are substantially linear. The surfactant can be incorporated in the element or added at the time of the assay.

19 Claims, 4 Drawing Sheets

ANALYTICAL ELEMENT AND METHOD FOR DETERMINATION OF TOTAL LACATE DEHYDROGENASE

RELATED APPLICATION

This is a continuation-in-part of Application Ser. No. 740,163 filed June 3, 1985, now abandoned.

FIELD OF THE INVENTION

This invention relates to clinical chemistry. In particular, it relates to a multilayer analytical element and a method of determination of total lactate dehydrogenase in aqueous liquids, e.g. biological fluids.

BACKGROUND OF THE INVENTION

The use of diagnostic tests in the clinical testing of patients has become increasingly common in recent years. For example the quantitative determination of lactate dehydrogenase (LDH) is extremely important in the detection of heart diseases. Following myocardial infarctions, the level of LDH in the blood rises noticeably over its normal concentration. The early detection of abnormal levels of LDH can therefore lead to a more accurate and rapid diagnosis of heart maladies.

Because early diagnosis of abnormal heart conditions is so important, a test for the detection of variation in LDH in the blood must be rapid and simple. It also must be highly accurate over a broad range of LDH concentrations encountered in patient testing.

A significant contribution in the field of clinical chemistry was the development of dry-to-the-touch multilayer analytical elements which could be used for simple, rapid and highly accurate testing of biological fluids. Such elements are described, for example, in U.S. Pat. Nos. 3,992,158 (issued Nov. 16, 1976 Przybylowicz et al) and 4,258,001 (issued Mar. 24, 1981 to Pierce et al). The Pierce et al reference, for example, describes multilayer elements comprising particulate spreading layers. These layers can also contain one or more surfactants to improve layer wettability.

European Patent Application 83/902727 (published Mar. 1, 1984 corresponding to PCT 84/00779) describes an assay for LDH carried out with a multilayer analytical element having a porous spreading layer containing a binder and microcrystalline cellulose (commercially available as Avicel ™ ). However, such elements containing microcrystalline cellulose spreading layers are difficult to manufacture on a large scale. Further, the assay described in this reference requires a blank subtraction step to reduce error. Hence, alternative materials were sought for making elements useful for LDH assays.

It was found that elements for LDH determination containing the beaded spreading layers described in the Pierce et al reference noted above are much easier to manufacture on a large scale than the Avicel ™ -containing elements. It was also found that the rate curves obtained in assays with these elements are more linear than the Avicel ™ -containing elements, even if no blank subtraction is made. However, it was observed that the assay of LDH with the Pierce et al elements was uunacceptably imprecise, especially at the lower levels of LDH. Blank subtraction does not eliminate this problem.

It would be highly desirable to have an element for LDH assay which is easily manufactured on a large scale, and which also exhibits acceptable precision over the entire range of LDH generally encountered in patient testing. It would also be desirable to avoid blank subtraction because it complicates the assay and requires additional equipment and computer software in automated analyzers.

SUMMARY OF THE INVENTION

I have found an analytical element and method for LDH determination that overcome the problems noted above. In particular, the assay of this invention is precise over the entire range of LDH concentrations generally encountered in patient testing, and particularly at the lower concentrations. Further, this improvement is achieved without a blank subtraction step because the response curves have improved linearity. The present invention is also unexpectedly less susceptible to interference by total protein and hemoglobin which may be in the test fluids. The improvements of this invention were achieved by the use of an analytical element comprising a particular fluorinated surfactant and a particulate spreading layer.

Therefore, in accordance with this invention, a dry analytical element for the determination of total lactate dehydrogenase (LDH) comprises a support having thereon, a porous spreading layer composed of a particulate structure comprising a plurality of particles being bonded to each other on surface areas of adjacent particles where the adjacent particles are in closest proximity to form a coherent, three dimensional lattice which is essentially non-swellable in an aqueous liquid, the element further comprising a saturated or unsaturated fluorinated surfactant having one or more fluorocarbon moieties, provided that when the surfactant contains more than one such moiety, the moieties are substantially linear.

This invention also provides a method for the determination of total LDH comprising the steps of:

A. in the presence of a substrate for LDH, an indicator material which provides a detectable change in response to the reaction of LDH with a substrate for LDH, and the fluorinated surfactant described above, contacting an analytical element with a sample of a liquid suspected of containing LDH, the element comprising a support having thereon a porous spreading layer composed of a particulate structure comprising a plurality of particles being bonded to each other on surface areas of adjacent particles where the adjacent particles are in closest proximity to form a coherent, three dimensional lattice which is essentially non-swellable in an aqueous liquid, and B. detecting the rate of the detectable change.

DETAILED DESCRIPTION OF THE INVENTION

Figure 1:
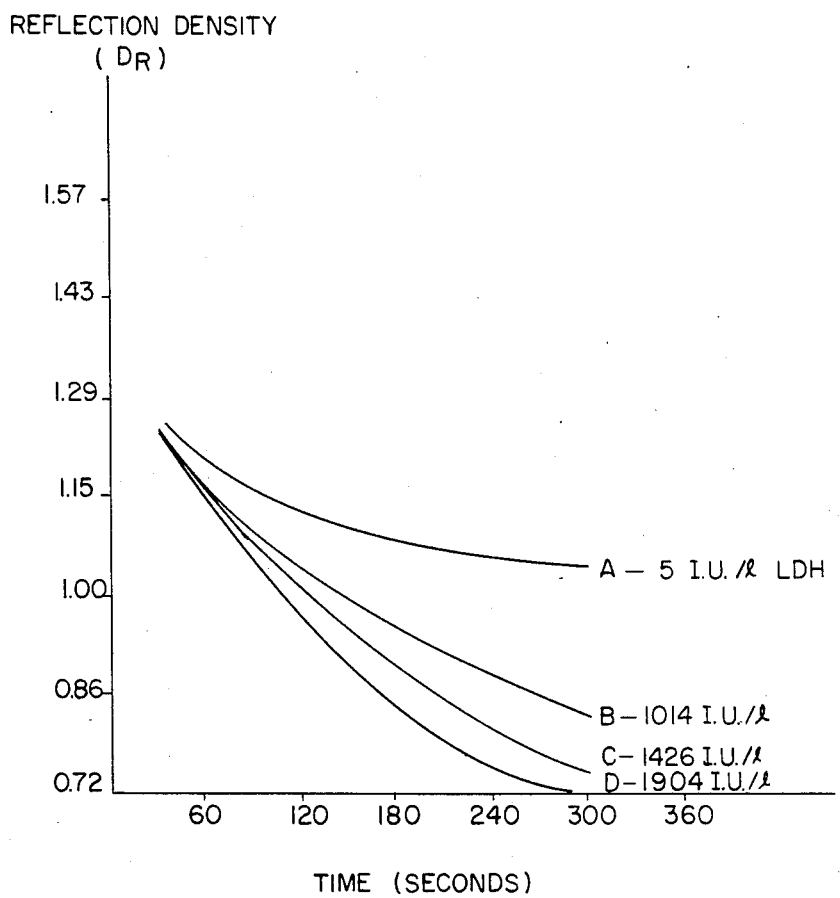
FIG. 1 is a graphical plot of the change in reflection density ($D_R$) with time for the determination of LDH using a prior art analytical element and several calibrator test fluids as described in Example 1 below.

The present invention can be used to advantage to determine the concentration of total lactate dehydrogenase (also known as L-lactate: NAD+ oxidoreductase, EC 1.1.1.27, or LDH herein) in an aqueous liquid, such as a biological fluid. LDH can be determined (i.e. qualitative, quantitative or semi-quantitative detection) in, for example, whole blood, blood serum, plasma, urine, spinal fluid, cerebral fluid, suspensions of human or animal tissue, feces, saliva, sputum, and other body fluids. Preferably, the assay of this invention is carried out with human whole blood or blood serum. LDH is known to exist in five isoenzymes (i.e. LDH-1, LDH-2, LDH-3, LDH-4 and LDH-5), all of which are determined collectively with the present invention.

The unexpected advantages of the present invention are achieved by the use of one or more fluorinated surfactants in the analytical element containing a particulate spreading layer described in more detail below. Useful surfactants can be anionic, cationic, nonionic or amphoteric. The molecule can have more than one charged moiety and either a net negative, positive or zero charge.

The useful surfactants are fluorinated, which means that the molecule contains one or more fluorocarbon moieties, each of which has one or more hydrogne atoms replaced by fluorine atoms. The remaining hydrogen atoms can be replaced with another substituent, if desired. Each fluorocarbon moiety generally has at least 4 carbon atoms. The fluorinated surfactant can be saturated or unsaturated. When the surfactant has two or more fluorocarbon moieties, these moieties are substantially linear, meaning that they are predominantly straight chain groups having no more than one or two small branches (e.g. methyl, fluorinated or unfluorinated). The moieties can be connected together by an organic backbone which is linear or branched. When the surfactant has only one fluorocarbon moiety, that moiety can be branched or linear.

Representative surfactants are listed below.

Nonionic Surfactants

Perfluoroalkylpoly(ethylene oxide) alcohols, for example, commercially available as ZONYL FSN from DuPont, (Wilmington, Del., U.S.A.), or as FLUOWET OT from American Hoechst (Charlotte, N.C.).

Cationic Surfactants

Perfluoroalkyl quaternary ammonium salts, for example, commercially available as Fluorad ® FC 135 from 3M Corporation, (St. Paul, Minn., U.S.A.), as LODYNE-106 from Ciba-Geigy (Ardsley, N.Y., U.S.A.) or an ZONYL FSC from DuPont.

Amphoteric Surfactants

Perfluoroalkyl betaines, for example, commercially available as SURFLON S-132 from Asahi Glass Co. (Japan), or as ZONYL FSK from DuPont, Fluoroalkylamino carboxylic acid, for example, commercially available as LODYNE-100 from Ciba-Geigy, (Ardsley, N.Y., U.S.A.).

Anionic Surfactants

Fluoroalkylsulfates, for example, FLUORTENSID FT-248 from Bayer (W. Germany) and FLUOWET SB from American Hoechst and fluoroalkylalkylenethioalkylenecarboxylates, for example ZONYL FSA from DuPont.

The Surflon TM S-132, FC-135 TM FLUOWET SB and ZONL FSA materials are preferred in the practice of this invention.

The amount of surfactant used in the practice of this invention will vary depending upon the particular surfactant chosen. However, generally the surfactant is present in the element in an amount sufficient to provide a precision in the assay of less than a standard deviation of about 30 I.U./l at LDH levels of about 5 to about 500 I.U./l, and less than about 5% CV at LDH concentrations from about 500 to about 2100 I.U./l. More preferably, the surfactant is present in an amount sufficient to provide a precision of less than about 11 I.U./l at the lower LDH levels, and less than about 3% CV at the higher LDH levels.

As used herein, the term precision refers to the random error observed in the assay at various LDH levels. This random error can be quantified with a term known in the art as "coefficient of variation". Coefficient of variation (CV) is defined as $\sigma \div \overline{X}$ times 100%, or the standard deviation "$\sigma$" about a mean $\overline{X}$ using a number of replicates.

The amount of fluorinated surfactant useful in this invention can also be defined generally in relation to the amount of LDH substrate used in the assay. Generally, the molar ratio of surfactant to substrate is from about 0.01:1 to about 10:1. Preferably, the molar ratio is from about 0.25:1 to about 2.5:1. Since the amount of surfactant will vary depending upon the particular surfactant used, the optimum molar ratio for each surfactant-substrate combination may vary in the entire broad range noted above. One particular surfactant may be especially useful at a 0.5:1 surfactant-substrate molar ratio, whereas a second surfactant may be especially useful at 2.0:1 ratio.

The fluorinated surfactant described herein can be incorporated into any or several layers of the element of this invention at the time of manufacture. For example, it can be in the particulate spreading layer, a subbing layer, a reagent layer, a registration layer, etc. as those layers are described below, or in two or more of such layers. Preferably, the surfactant is in reactive association with the substrate (described below). This means that the surfactant and substrate are in the same layer, or individually in layers close enough that they interact during the assay. The surfactant and substrate can be individually incorporated in the element during manufacture, or added separately or together at the time of assay. Most preferably, the surfactant is in the particulate spreading layer with the substrate.

LDH is determined in the practice of this invention as a result of the activity of the enzyme on a suitable substrate to produce a detectable change over a period of time. The detectable change can be a signal that increases with time, e.g. an increasing amount of potentiometric or spectrophotometric signal (such as millivolt response, fluorometric or colormetric). Alternatively, the detectable change can be a signal which decreases with time such as when a detectable species is destroyed or converted into a non-detectable species. In the following discussions, preferred changes in fluorescent signals are emphasized in the practice of this invention.

The analytical element of this invention can be manufactured with incorporation of the appropriate reagents for the assay of LDH according to either the forward or reverse reaction illustrated in the following equation:

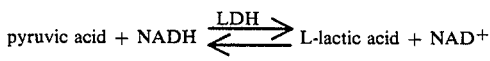

wherein NADH is nicotinamide adenine dinucleotide, reduced form. The forward reaction is preferred in the practice of this invention. In either case, the substrate is the noted acid or a suitable alkali or ammonium salt thereof. The reagents can also be added to the element just prior to or during the assay.

When incorporated into the element, the substrate can be present anywhere in the element in an amount which can be readily determined by a skilled clinical chemist. Preferably, the substrate is present in the spreading layer (described below) in an amount of at least about 0.01, and preferably from about 0.05 to about 2, g/m$^2$. Suitable substrates are readily available commercially from a number of sources.

The element of this invention can also be manufactured with incorporation of an indicator material located in any suitable layer of the element. Generally the indicator material is located in the registration layer (descibed below). The indicator material is either NADH or NAD$^+$ depending upon which of the reactions of the equation above is used in the assay. This material is present in an amount readily known to a skilled clinical chemist. Preferably, it is present in stoichiometric excess. The element can contain other reagents which can react with either NADH or NAD$^+$ in one or more enzymatic or nonenzymatic reactions to produce a detectable signal, e.g. color dye, fluorescence, chemiluminescence, potentiometric change, etc. For example, NADH can be reacted with a tetrazolium salt to produce a colored dye as described, for example, in U.S. Pat. No. 3,867,258 (issued Feb. 18, 1975 to Forgione). The indicator materials and other reagents which may be used in this invention can be readily obtained commercially from a number of sources or prepared using known techniques and starting materials.

The element can also contain other suitable addenda commonly included therein to facilitate the assay, including buffers, surfactants (other than the fluorinated compounds noted above), binders and hardeners. The assay of this invention is generally carried out at a suitable pH, e.g. from about 5 to about 9. Therefore, it is desirable to include one or more suitable buffers in one or more layers of the element to maintain the desired pH during the assay. Useful buffers are well known to one of ordinary skill in the art.

The assay of this invention can be successfully carried out with a dry analytical element having a support and only one layer thereon. This layer is a porous spreading layer having suitable porosity for accomodating a test sample, diluted or undiluted. Preferably, the spreading layer is isotropically porous, which property is created by interconnected spaces between the particles comprising the layer. By isotropically porous is meant that the spreading layer uniformly spreads the applied test sample radially throughout the layer.

Various types of particulate matter, all essentially non-swellable in and chemically inert and impermeable to the liquid components, are useful for forming a spreading layer including, for example, pigments (e.g. titanium dioxide, barium sulfate, etc.), diatomaceous earth, colloidal materials, resinous or glass beads and the like. These particulate materials can be distributed in a suitable binder, e.g. a colloidal or polymeric material, as is known in the art (e.g. U.S. Pat. No. 3,992,158, noted above). The amount of binder can be varied depending upon the type of binder used and the amount of particulate material in the spreading layer.

Examples of other useful particulate materials which can be formed into particulate structures include the polymer particles described in U.S. Pat. No. 4,430,436 (issued Feb. 7, 1984 to Koyama et al), which particles are chemically bound to each other through reactive groups incorporated in the particles at the points of particle contact. Other useful polymer particles are described in Japanese Patent Publication 57(1982)-101760 (published June 24, 1982), which particles are chemically bound to each other at points of contact with a low molecular weight adhesive compound (e.g. reaction products of bisphenols, dicarboxylic acids, or amino compounds, etc.).

Particularly useful spreading layers are those having a particulate structure formed by organo-polymeric particles and a polymeric adhesive for those particles as described, for example, in U.S. Pat. No. 4,258,001 (noted above). Maintaining particulate integrity of the organo-polymeric particles in the particulate structure with the polymeric adhesive prevents the coalescence and flow of the particles into the voids, and the concentration of adhesive at those particle surface areas of the structure which are contiguous to adjacent particles insures that the adhesive does not flow into and clog the voids.

Materials which can be used to prepare the spreading layers preferred in the practice of this invention are described in considerable detail in the Pierce et al patent noted above. Therefore, the present disclosure is directed to a general description of the layer while noting preferred embodiments of this invention. The thickness of the described particulate structure can be varied depending upon the size of the organo-polymeric particles and can be readily determined by one of ordinary skill in the art.

The heat-stable, organo-polymeric particles useful in the practice of this invention are generally spherical beads having a particle size in the range of from about 1 to about 200 $\mu$m in diameter. Preferably, they have a particle size within the range of from about 10 to about 60 $\mu$m in diameter. Particles of this size provide the appropriate capillary action and test sample retention time which allows the desired reactions to occur.

The particles can be composed of a wide variety of organic polymers, including both natural and synthetic polymers, having the requisite properties. Preferably, however, they are composed of one or more addition polymers formed from one or more ethylenically unsaturated polymerizable monomers, such as addition homopolymers of single monomers or copolymers formed from two or more such monomers. These polymers can be prepared by any of a variety of standard polymerization methods (e.g. solution, emulsion, dispersion, suspension, etc.). If desired, although the invention is not so limited, the particular polymer can contain one or more reaction sites to link various interactive compositions to the particles.

Particularly useful addition polymers are those formed by polymerizing one or more of the following ethylenically unsaturated polymerizable monomers, the details of which are provided in the Pierce et al patent noted above:

(a) from 0 to 100, preferably from 0 to about 99, weight percent of one or more amino-substituent-free vinyl carbocyclic aromatic monomers, including the styrene monomers described in the Pierce et al patent, as well as similar amino-substituent-free vinyl naphthyl monomers, (b) from 0 to about 25 weight percent of one or more acrylic acid esters, (c) from 0 to 100, preferably 0 to about 75, weight percent of one or more methacrylic acid esters, (d) from 0 to about 30 weight percent of one or more ethylenically unsaturated carboxylic acids.

(e) from 0 to about 75 weight percent of one or more ethylenically unsaturated nitrile, (f) from 0 to about 20 weight percent of one or more amino-substituted vinyl carbocyclic aromatics, including the styrene monomers described in the Pierce et al patent, as well as similar amino-substituted vinyl naphthyls, (g) from 0 to about 20, preferably 0 to about 10, weight percent of one or more ethylenically unsaturated crosslinkable monomers, including those which can be crosslinked with amines or gelatin hardeners and those having two or more ethylenically unsaturated polymerizable groups, (h) from 0 to about 20 weight percent of one or more tertiary aminoalkyl acrylates or methacrylates, (i) from 0 to 100, preferably 0 to about 75, weight percent of one or more polymerizable, N-heterocyclic vinyl monomers, and (j) from 0 to about 20 weight percent of one or more acrylamides or methacrylamides.

Particularly useful addition polymers include those listed in Table I of the Pierce et al patent. The numbers in the brackets represent the weight ratio of monomers in the monomer blend used to prepare the polymer. Poll(vinyltoluene-co-p-t-butylstyrene-co-methacrylic acid) [61:37:2], poly(styrene-co-n-butyl acrylate) [75:25] and polystyrene are preferred polymers. The organo-polymeric particles can contain other addenda, if desired, as known in the art.

The polymeric adhesive which is useful in this invention bonds the organo-polymeric particles to one another to provide a coherent, three-dimensional lattice in the spreading layer. The details of particular adhesives are provided in the Pierce et al patent, noted above. Generally, the adhesive is composed of an organic polymer different from the specific polymer contained in the particles, although quite commonly the adhesive represents a polymer containing many repeating units which are identical or similar to some of those present in the polymer composition of the particles.

Preferably, the adhesive is composed of one or more addition polymers formed from one or more ethylenically unsaturated polymerizable monomers, such as addition copolymers formed from two or more of such monomers. Like the particles, the adhesive can be prepared by any of a variety of conventional polymerization methods.

Generally, the amount of adhesive contained in the particulate structure is less than about 10 percent to provide optimum adhesion and liquid spreading time, based on the weight of the particles.

Particularly useful addition polymers employed as adhesives are formed by polymerizing a blend of ethylenically unsaturated polymerizable monomers selected from the blends described as follows, the details of which are provided in the Pierce et al patent noted above:

A. a blend containing from about 1 to about 35, preferably from about 10 to about 30, weight percent of one or more amino-substituent-free vinyl carbocyclic aromatics as described above, and from about 65 to about 99, preferably from about 70 to about 90, weight percent of one or more alkyl acrylates or methacrylates, B. a blend containing from about 20 to about 95, preferably from about 50 to about 95, weight percent of one or more amino-substituent-free vinyl carbocyclic aromatics, acrylic or methacrylic acid esters and ethylenically unsaturated polymerizable crosslinkable monomers, and from about 5 to about 80, preferably from about 5 to about 50, weight percent of one or more ethylenically unsaturated polymerizable monomers having an active hydrogen or salts thereof., C. a blend containing from about 15 to 100 weight percent of one or more ethylenically unsaturated monomers selected from the group consisting of 1-vinylimidazole, N-vinyl-2-pyrrolidone, vinylbenzyl alcohol, ethyl acrylate or an acrylamide or methacrylamide, and from 0 to about 85 weight percent of one or more ethylenically unsaturated polymerizable crosslinkable monomers, and D. a blend containing from about 80 to about 98, and preferably from about 85 to about 98, weight percent of one or more acrylic or methacrylic acid esters, and from about 2 to about 20 and preferably from about 2 to about 15, weight percent of one or more ehtylenically unsaturated polymerizable monomers containing one or more anionic moieties (e.g. carboxy, sulfino, sulfo, phosphono, etc. or alkali metal or ammonium salts thereof).

Particularly useful addition polymers include those listed in Table II of the Pierce et al patent and in U.S. Pat. No. 4,283,491 (issued Aug. 11, 1981 to Dappen). The numbers in the brackets represent the weight ratio of monomers in the monomer blend used to prepare the polymer. Poly(methyl acrylate-co-2-acetoacetoxyethyl methacrylate-co-2-acrylamido-2-methylpropanesulfonic acid) [88:7:5], poly(N-isopropylacrylamide), poly(n-butyl acrylate-co-styrene-co-2-acrylamido-2-methylpropane sulfonic acid, sodium salt) [70:20:10] and poly(N-vinyl-2-pyrrolidone) are preferred adhesive polymers.

Various methods can be employed for preparing the particulate structure with the above-described particles and adhesives. Specific details of useful methods are provided in the Pierce et al patent noted above.

The spreading layer of the element of this invention is carried on a suitable support. Such a support can be any suitable dimensionally stable, and preferably, nonporous and transparent (i.e. radiation transmissive) material which transmits electromagnetic radiation of a wavelength between about 200 and about 900 nm. A support of choice for a particular element should be compatible with the intended mode of detection (e.g. reflection or transmission spectroscopy or fluorimetry). Useful support materials include polystyrene, polyesters [e.g. poly(ethylene terephthalate)], polycarbonates, cellulose esters (e.g. cellulose acetate), etc.

In a preferred embodiment, the element of this invention also comprises a second layer, sometimes known as a reagent or a registration layer, which contains the indicator material (e.g. NADH) described above. Generally, the second or registration layer is immediately adjacent the support although an optional subbing layer for adhesive purposes can be interposed, if desired. The layers of the element are generally in fluid contact with each other, meaning that fluids and reagents and reaction products in the fluids can pass between superposed regions of adjacent layers.

The second or registration layer of the element is preferably nonparticulate, meaning that it is essentially free of particulate material as compared to the spreading layer. It generally contains one or more synthetic or natural binder materials, such as gelatin (hardened or unhardened), or other naturally-occurring colloids, polysaccharides, homopolymers and copolymers, such as poly(acrylamide), poly(N-vinyl-2-pyrrolidone), poly(n-isopropylacrylamide), poly(acrylamide-co-N-vinyl-2-pyrrolidone) and similar copolymers.

The element of this invention also optionally contains one or more other layers including subbing layers, radiation-blocking layers, other spreading layers underneath the beaded spreading layer described above, reagent layers, etc. as known in the art, e.g. as described in U.S. Pat. Nos. 3,992,158 and 4,258,001, noted above.

The present invention can be performed with any analyzer constructed to perform rate assays, that is, to examine each test sample more than once over a period of time so that the rate of detectable change can be determined.

The assay of this invention can be manual or automated. In general, the amount of LDH in a liquid sample is determined by taking the element from a supply roll, chip packet or other source and physically contacting the spreading layer of the element with a sample of the liquid (e.g. 1 to 200 μl). Contact of the element and sample can be accomplished in any suitable manner, e.g. by dipping the element in the liquid sample or by spotting the spreading layer by hand or machine with a drop of the sample by pipette or other suitable dispensing means. If any one or both of the substrate, indicator material or fluorinated surfactant is not incorporated in the element during manufacture, they can be applied to the element in a similar fashion, separately or together.

After sample-element contact, the element is exposed to any conditioning, such as incubation, heating or the like, that may be desirable to quicken ot otherwise facilitate obtaining the test result.

The LDH determination is made by passing the element through a suitable apparatus for detecting the detectable change whether it be a potentiometric or spectrophotometric change. Preferably, the determination is made by determining the rate of disappearance of colorimetric signal (e.g. absorption) due to the reaction of NADH with pyruvic acid to form NAD+ and lactic acid. The amount of LDH can be correlated through first order kinetics to the rate measured in the assay using standard procedures and calculations.

The following examples are provided to illustrate the practice of the present invention. In these examples, the materials used were obtained as follows:

Lactate dehydrogenase from Sigma Chemical Co. (St. Louis, Mo., U.S.A.),

NADH from P.L. Biochemical Co. (Milwaukee, Wis., U.S.A.),

TRITON X-100 and X-405 nonionic surfactants from Rohm and Haas (Philadelphia, Pa., U.S.A.), Poly(N-vinyl-2-pyrrolidone) from GAF Corp. (New York, N.Y., U.S.A.), ZONYL FSN, ZONYL FSA, ZONYL FSK, and ZONYL FSC surfactants from DuPont (Wilmington, Del., U.S.A.), MONFLUOR 31 and 51 surfactants from ICI (Wilmington, Del., U.S.A.), FC 135 TM cationic surfactant from 3M Company (St. Paul, Minn., U.S.A.), FLUORTENSID FT-248 anionic surfactant from Bayer (W. Germany), FLUOWET SB anionic surfactant from American Hoechst (Charlotte, N.C., U.S.A.), SURFLON S-132 amphoteric surfactant from Asahi Glass Co. (Japan), AVICEL from FMC Corp. (Philadelphia, Pa., U.S.A.), LODYNE-106 and -100 cationic and amphoteric surfactants, respectively, from Ciba-Geigy (Ardsley, N.Y., U.S.A.), and the remainder from Eastman Kodak Company (Rochester, N.Y.) or prepared using known starting materials and synthetic procedures.

As used in the context of this disclosure, I.U. represents the International Unit for enzyme activity defined as one I.U. being the amount of enzyme activity required to catalyze the conversion of 1 micromole of substrate per minute under standard pH and temperature conditions for the enzyme.

EXAMPLE 1

Analytical Element for the Determination of Total LDH

This is a comparative example comparing an element of the prior art to an element of the present invention.

An element of the prior art (see E.P.A. 83/902727 noted above) was prepared having the following format and components:

| | | |
|---|---|---|
| Spreading Layer | Microcrystalline cellulose (AVICEL) | 30–80 g/m$^2$ |
| | Poly(N—vinyl-2-pyrrolidone) | 0.5–2 g/m$^2$ |
| | N—tris(hydroxymethyl)-methyl-2-aminoethane sulfonic acid (pH 7.3) | 0.05–0.2 g/m$^2$ |
| | Sodium pyruvate | 0.05–0.2 g/m$^2$ |
| Registration Layer | Gelatin (hardened) | 5–20 g/m$^2$ |
| | TRITON X-405 surfactant | 0.5–2.5 g/m$^2$ |
| | N—tris(hydroxymethyl)-methyl-2-aminoethane sulfonic acid (pH 7.3) | 0.5–2 g/m$^2$ |
| | NADH | 0.1–0.8 g/m$^2$ |
| | Poly(ethylene terephthalate) Support | |

An element of the present invention was prepared having the following format and components:

| | | |
|---|---|---|
| Spreading Layer | Poly(vinyltoluene-co-p-t-butylstyrene-co-methacrylic acid) (61:37:2 weight ratio) beads | 100–200 g/m$^2$ |
| | Poly(N—isopropylacrylamide) | 0.1–2 g/m$^2$ |
| | Sodium pyruvate | 0.01–2 g/m$^2$ |
| | N—tris(hydroxymethyl)-methyl-2-aminoethane sulfonic acid (pH 7.3) | 0.05–0.5 g/m$^2$ |

| | | |
|---|---|---|
| | -continued | |
| | SURFLON S-132 fluori-<br>nated surfactant | 0.1–10 g/m² |
| | Poly(N—vinyl-2-pyrrolidone) | 0.1–2 g/m² |
| Registration | Gelatin (hardened) | 5–20 g/m² |
| Layer | TRITON X-100 surfactant | 0.05–1 g/m² |
| | N—tris(hydroxymethyl)-<br>methyl-2-aminoethane<br>sulfonic acid (pH 7.3) | 0.5–2.5 g/m² |
| | NADH | 0.1–0.8 g/m² |
| | Poly(ethylene terephthalate)<br>Support | |

The element of the prior art described above was used to determine total LDH in several calibrator fluids by spotting the element with a 10 μl sample of each fluid. The amount of LDH (I.U./l) was determined by measuring the change in reflection density ($D_R$) at 340 nm with time (seconds) after incubation at 37° C. using a commercially available spectrophotometer. No blank subtraction step was made in generating the response curves shown in FIG. 1. FIG. 1 shows the non-linear curves obtained with each of the sample fluids A-D (5, 1014, 1426 and 1904 I.U./l, respectively).

Figure 2:
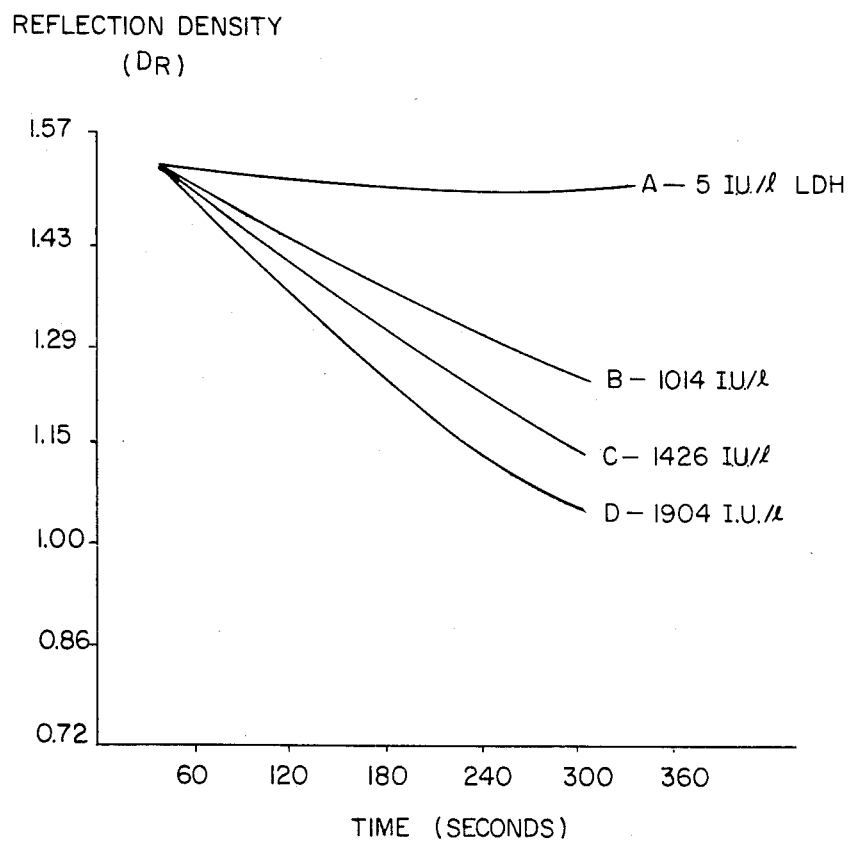
FIG. 2 is a graphical plot of the change in reflection density ($D_R$) with time for the determination of LDH using the analytical element of this invention and several calibrator test fluids as described in Example 1 below.

The same tests were performed on the same day on an element of the present invention described above. No blank subtraction step was made in generating the response curves shown in FIG. 2. FIG. 2 shows the resulting response curves which are more linear than those shown in FIG. 1.

EXAMPLE 2

Analytical Elements Containing Various Surfactants

Several analytical elements were prepared having the format and components of the element of the invention shown in Example 1 except that various surfactants were incorporated into the spreading layer. The particular surfactants used are shown in Table I below. They were present within a range of about 0.5:1 to about 2:1 molar ratio of surfactant to sodium pyruvate substrate.

TABLE I

| Element | Surfactant | Amount in Element (g/m²) |
|---|---|---|
| 1 | LODYNE-100 | 0.33–0.99 |
| 2 | SURFLON S-132 | 0.36–1.4 |
| 3 | FC-135 TM | 0.33–1.1 |
| 4 | LODYNE-106 | 0.34–1 |
| 5 | ZONYL FSN | 0.33–0.99 |
| Control 1 | MONFLOR 51* | 0.33–1.9 |
| Control 2 | TRITON X-100** | 1.1 |
| Control 3 | Hexyldecyltrimethyl-<br>ammonium bromide | 0.18–0.53 |

*Fluorinated surfactant having two unsaturated and branched fluorocarbon moieties.
**Nonionic nonfluorinated surfactant.

Figure 3:
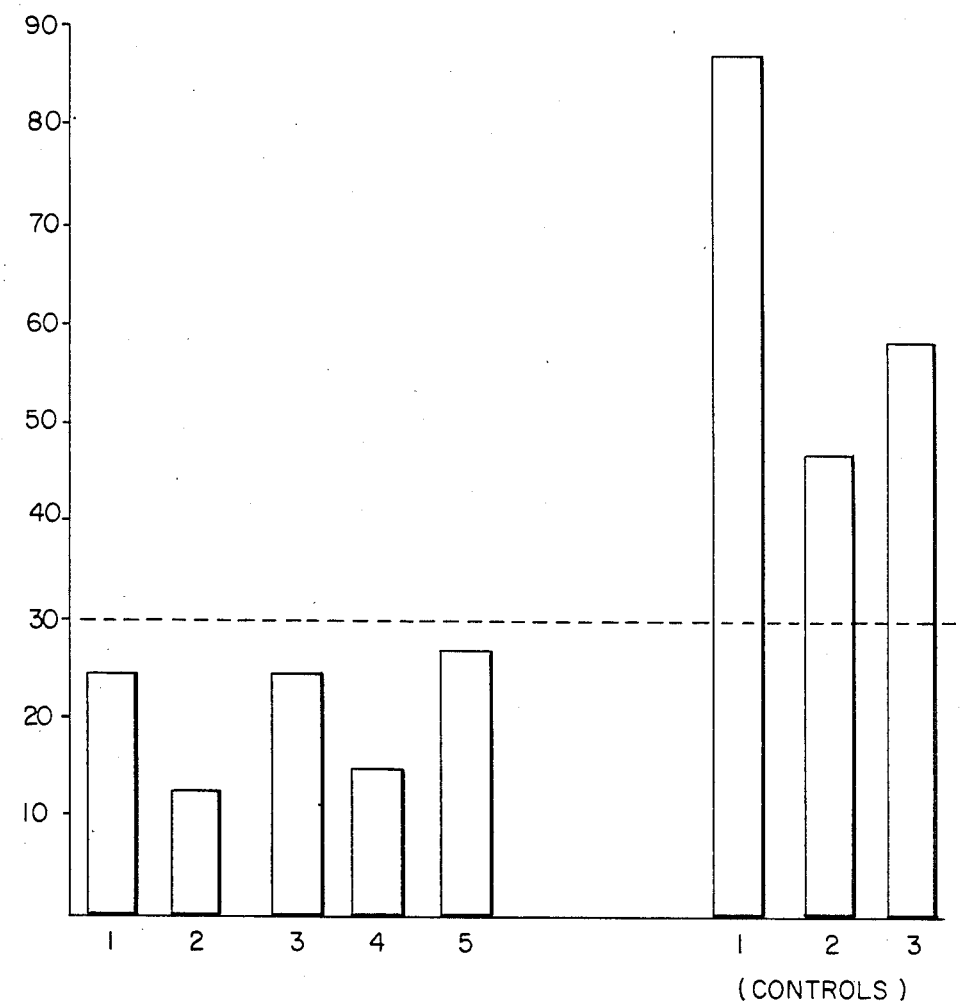
FIG. 3 is a bar graph showing the effect of various surfactants on LDH assay precision using a 5 I.U./l LDH test fluid as described in Example 2 below.
Figure 4:
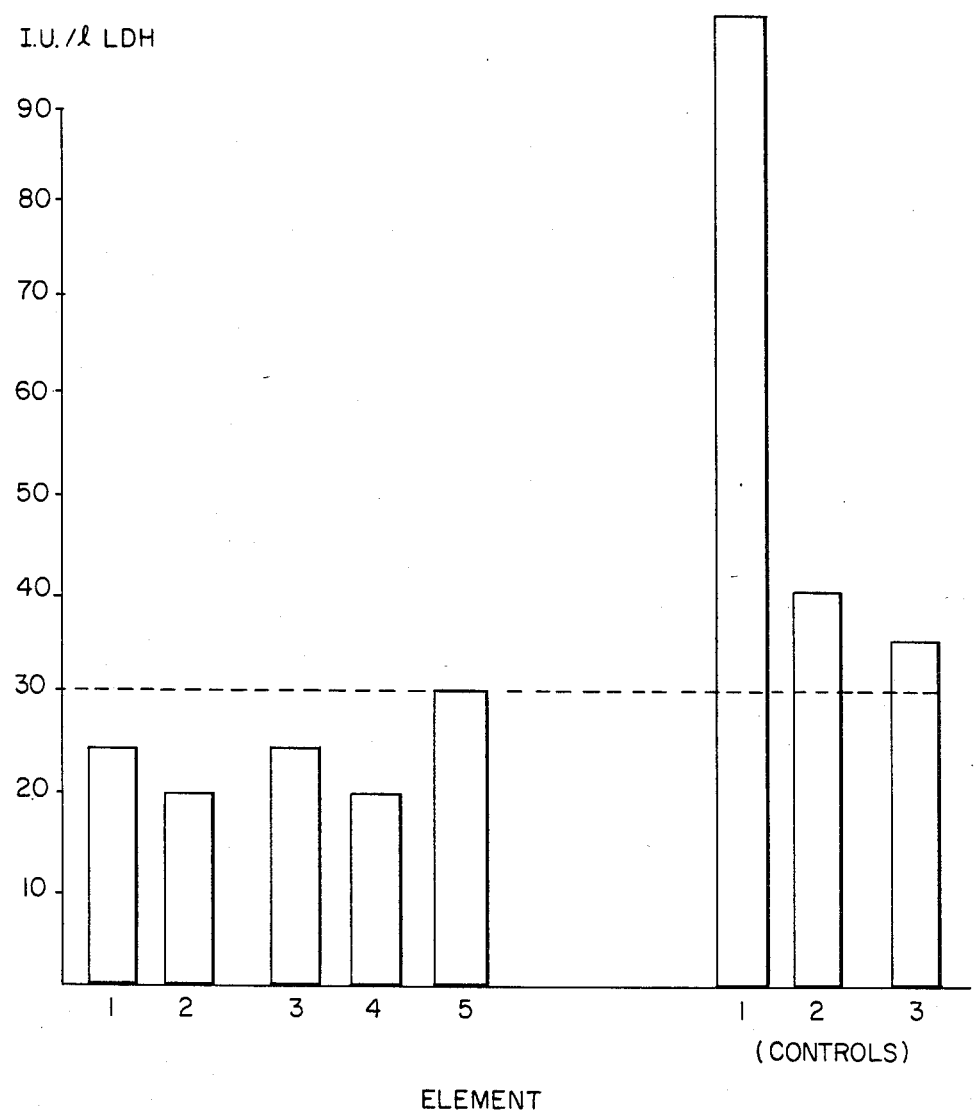
FIG. 4 is similar to FIG. 3 except that a 464 I.U./l LDH test fluid was used as described in Example 2 below.

Each element was spotted with a 10 μl aliquot of each of two test fluids containing 5 and 464 I.U./l LDH, respectively. LDH was determined as described in Example 1. From the resulting data, standard deviations, $\sigma$, in I.U./l were determined for each test fluid and element. FIGS. 3 and 4 are bar graph plots of the average mean $\sigma$ for each element and the two test fluids, respectively, across all concentrations of each surfactant used. The acceptable $\sigma$ at these LDH levels, as expressed in I.U./l, is about 30 I.U./l with less than about 11 I.U./l being the preferred $\sigma$. These $\sigma$ values can be converted to % CV as described above. It can be seen that the assays performed with the Control elements 1–3 did not exhibit acceptable precision. Control 2 is an element prepared according to U.S. Pat. No. 4,258,001, noted above. The assays carried out with the elements (1–5) prepared according to this invention exhibited acceptable precision. These tests were made with a blank subtraction step. The same improvement is obtained without a blank subtraction step.

EXAMPLE 3

LDH Assay and Precision Results

A preferred element prepared according to Example 1 containing SURFLON S-132 surfactant in the beaded spreading layer was used to determine LDH over a wide range of LDH concentrations (5–1904 I.U./l). The actual precision, $\sigma$ (I.U./l) for the low LDH level test fluid determined from the assay and the % CV for the higher LDH test fluids, are given in Table II below. At the low LDH concentration, it is known in the art to measure precision with $\sigma$ since the % CV calculated at those concentrations would be meaningless. For the low concentration, acceptable precision is a $\sigma$ of about 30 I.U./l or less. At the higher concentrations, acceptable precision is about 5% CV or less. These data were obtained with a blank subtraction step.

TABLE II

| Test Fluid (I.U./l) | Actual Precision |
|---|---|
| 5 | 4.6 ($\sigma$) |
| 1014 | 2.0% CV |
| 1426 | 2.0% CV |
| 1904 | 0.8% CV |

An element similar to that described above in this example was used to determine LDH over another range of LDH concentrations (203–2065 I.U./l) using the same procedure except no blank subtraction step was used in the assay. Table III below contains the actual precision of these determinations. Acceptable precision was achieved in each assay.

TABLE III

| Test Fluid (I.U./l) | Actual Precision |
|---|---|
| 203 | 5.6 ($\sigma$) |
| 650 | 0.7% CV |
| 2065 | 0.7% CV |

EXAMPLE 4

LDH Assay Exhibiting Reduced Interference

The prior art element and element of this invention shown in Example 1 were evaluated for susceptibility to interferences. Each element was spotted with a 10 μl aliquot sample of pooled human serum which had been treated with the potential interferents noted in Table IV below. The elements were tested according to the procedure described in Example 1 and the adverse effect of the interferents were determined. The deviation (Δ) from a reference LDH value is a measure of the effect of the interferent. An acceptable Δ is ±49 I.U./l. The results of the tests with both elements are shown in Table IV below.

TABLE IV

| Interferent | Concentration (g/dl) of Interferent | (Δ) Prior Art Element | (Δ) Element of Invention |
|---|---|---|---|
| Total Protein | 3.9 | +25 | −2 |
| Total Protein | 6.4 | +70 | −7 |

TABLE IV-continued

| Interferent | Concentration (g/dl) of Interferent | (Δ) Prior Art Element | (Δ) Element of Invention |
|---|---|---|---|
| Total Protein | 10.0 | +144 | −17 |
| Hemoglobin | .15 | +82 | −30 |
| Hemoglobin | .05 | +33 | −16 |

The data illustrate the improvement obtained with the present invention using the element containing the fluorinated surfactant in a beaded spreading layer. The element of this invention is less susceptible to interference by total protein and hemoglobin.

EXAMPLE 5

Analytical Elements Containing Various Fluorinated Surfactants

Several analytical elements were prepared having the format and components of the element of the invention shown in Example 1 except that various fluorinated surfactants were incorporated into the spreading layer at about 1:1 molar ratio to the substrate.

Each element was spotted with a 10 μl sample of each of two test fluids containing 218 and 2325 I.U./l lactate dehydrogenase, respectively. The analyte was determined as described in Example 1, and precision data in the form of standard deviation ($\sigma$) or % CV were calculated. Table V below lists the surfactants tested and the resulting data. All elements demonstrated acceptable precision in these tests.

TABLE V

| Surfactant | $\sigma$ with 218 I.U./l Test Fluid | % CV with 2325 I.U./l Test Fluid |
|---|---|---|
| ZONYL FSK | 20.0 | 1.3 |
| ZONYL FSC | 14.2 | 0.7 |
| FLUORTENSID FT-248 | 19.4 | 0.4 |
| ZONYL FSA | 3.8 | 0.6 |
| MONFLOR 31 | 20.4 | 1.0 |

EXAMPLE 6

Various Coverages of Fluorinated Surfactant

A series of elements were prepared like the element of the present invention shown in Example 1. The SURFLON S-132 surfactant was included in the elements of various coating coverages. In a Control element, the fluorinated surfactant was omitted. The elements were tested with test fluids having 203 and 1918 I.U./l of lactate dehydrogenase, respectively, according to the procedure described in Example 1. The precision results, either in standard deviation ($\sigma$) or % CV, are presented in Table VI below. All elements containing the surfactant exhibited acceptable precision. The Control element exhibited unacceptable precision with the low LDH test fluid.

TABLE VI

| Surfactant Level (g/m$^2$) | $\sigma$ with 203 I.U./l Test Fluid | % CV with 1918 I.U./l Test Fluid |
|---|---|---|
| 0 (Control) | 58.3 | 3.3 |
| 0.037 | 12.0 | 1.9 |
| 0.187 | 3.5 | 0.9 |
| 0.37 | 2.4 | 0.7 |
| 0.74 | 12.4 | 0.9 |

EXAMPLES 7-9

Various Element Formats

Several analytical elements of the invention were prepared and tested as described in Example 1 using 203 and 1918 I.U./l lactate dehydrogenase test fluids. The elements and assays varied from that described in Example 1 in the following ways:

Element 7: Sodium pyruvate was placed in the registration layer and omitted from the spreading layer.

Element 8: Contained no sodium pyruvate. It was added to the element at the same time the test fluid was applied.

Element 9: Contained no NADH. It was added to the element at the same time the test fluid was applied.

Table VII below shows the acceptable precision results obtained with these test elements.

TABLE VII

| Element | $\sigma$ with 203 I.U./l Test Fluid | % CV with 1918 I.U./l Test Fluid |
|---|---|---|
| 7 | 5.5 | 1.2 |
| 8 | 8.2 | 0.6 |
| 9 | 3.1 | 1.0 |

EXAMPLE 10

Analytical Element for the Determination of Total LDH

This is a comparative example comparing an element of the present invention containing a fluorinated surfactant having two substantially linear fluorocarbon moieties to an element outside of the present invention containing a fluorinated surfactant having two highly branched fluorocarbon moieties.

An element of the present invention was prepared having the following format and components:

| | | |
|---|---|---|
| Spreading Layer | Poly(vinyltoluene-co-p-t-butylstyrene-co-methacrylic acid) (61:37:2 weight ratio) beads | 100-200 g/m$^2$ |
| | Poly(N—isopropylacrylamide) | 0.1-2 g/m$^2$ |
| | Sodium pyruvate | 0.01-2 g/m$^2$ |
| | N-tris(hydroxymethyl)-methyl-2-aminoethane sulfonic acid (pH 7.3) | 0.05-0.5 g/m$^2$ |
| | FLUOWET SB fluorinated surfactant | 0.1-10 g/m$^2$ |
| | Poly(N—vinyl-2-pyrrolidone) | 0.1-2 g/m$^2$ |
| Registration Layer | Gelatin (hardened) | 5-20 g/m$^2$ |
| | TRITON X-100 surfactant | 0.05-1 g/m$^2$ |
| | N—tris(hydroxymethyl)-methyl-2-aminoethane sulfonic acid (pH 7.3) | 0.5-2.5 g/m$^2$ |
| | NADH | 0.1-0.8 g/m$^2$ |
| | Poly(ethylene terephthalate) Support | |

A Control element was similarly prepared except that FLUOWTET SB was replaced with 1.9 g/m$^2$ of MONFLOR 51 which is fluorinated surfactant having the structure:

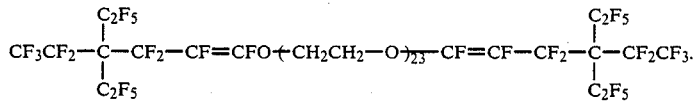

FLUOWET SB has the structure:

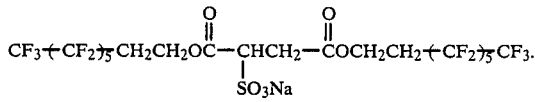

Both elements were used to determine total LDH in several test fluids (containing various levels of LDH) by spotting the element with 10 μl sample of each fluid. The amount of LDH (I.U./l) was determined by measuring the change in reflection density ($D_R$) at 340 nm with time (seconds) after incubation at 37° C. using a standard spectrophotometer. No blank subtraction step was made.

From the resulting data, precision of the respective assays was determined by calculating standard deviations, σ, for the test fluids having less than 500 I.U./l LDH. For the test fluids having more than 500 I.U./l LDH, a % CV was calculated as described above. The results are shown in Table VIII below.

TABLE VIII

| Test Fluid (I.U./l LDH) | Control Element (σ or % CV) | Example Element (σ or % CV) |
|---|---|---|
| 5 | 85.6 (σ) | NA |
| 218 | NA | 4.5 (σ) |
| 464 | 116.2 (σ) | NA |
| 697 | NA | 1.8% |
| 1904 | 7.9% | NA |
| 2325 | NA | 0.6% |

NA = not available

It can be seen that the Control element did not exhibit acceptable precision in the assay for LDH at any LDH level it was tested at. In contrast, the element of the present invention provided high precision in the assay at both low and high LDH levels. While the elements were not tested with the same test fluids, the comparison is nonetheless clinically acceptable because above 1900 I.U./l, the difference between 1904 and 2325 is clinically insignificant in measuring this analyte. The Control element was unacceptable over the entire range of LDH concentrations. It is reasonable to believe that the precision would have been unacceptable at 218 I.U./l for the Control element since it was unacceptable at both 5 and 464 I.U./l.

The invention has been described in detail with particular reference to preferred embodiments thereof, but it will be understood that variations and modifications can be effected within the spirit and scope of the invention.

I claim:

1. A dry analytical element for the determination of total lactate dehydrogenase (LDH) comprising a support having thereon
   a porous spreading layer composed of a particulate structure comprising a plurality of particles being bonded to each other on surface areas of said particles which are adjacent, where said adjacent particles form a coherent, three dimensional lattice which is essentially non-swellable to an aqueous liquid,
   said element further comprising a saturated or unsaturated fluorinated surfactant containing one or more fluorocarbon moieties each having from 4 to 16 carbon atoms and from 8 to 33 fluorine atoms, and each of said moieties having a ratio of fluorine atoms to carbon atoms of about 2:1, provided that when said surfactant contains more than one such moiety, said moieties have up to two fluorinated or unfluorinated methyl branches.

2. The element of claim 1 further comprising a substrate for LDH wherein the molar ratio of said fluorinated surfactant to said substrate is from about 0.01:1 to about 10:1.

3. The element of claim 2 wherein the molor ratio of said fluorinated surfactant to said substrate is from about 0.25:1 to about 2.5:1.

4. The element of claim 1 further comprising a second layer containing an indicator material which provides a detectable spectrophotometric change in response to the reaction of LDH with said substrate.

5. The element of claim 1 wherein said fluorinated surfactant is located in said spreading layer.

6. The element of claim 1 wherein said surfactant has only one fluorocarbon moiety.

7. A dry multilayer analytical element for the determination of total lactate dehydrogenase (LDH), said element comprising a support having thereon, in order from said support and in fluid contact,
   a registration layer comprising an indicator material which provides a detectable spectrophotometric change in response to the reaction of LDH with a substrate for LDH, and
   an isotropically porous spreading layer comprising said LDH substrate and composed of a particulate structure comprising:
   (i) a plurality of heat-stable, organo-polymeric particles non-swellable in and impermeable to an aqueous liquid, and having a particle size of from about 1 to about 200 μm, and
   (ii) an adhesive, in an amount of up to about 10 weight percent of said particles, comprising an organic polymer different from that of said particles,
   substantially all of said adhesive being concentrated on surface areas of adjacent particles where said adjacent particles are in closest proximity, and bonding said particles into a coherent, three-dimensional lattice which is essentially non-swellable in said liquid,
   said element containing, in any of said layers, a saturated or unsaturated fluorinated surfactant containing one or more fluorocarbon moieties each having from 4 to 16 carbon atoms and from 8 to 33 fluorine atoms, and each of said moieties having a ratio of fluorine atoms to carbon atoms of about 2:1, provided that when said surfactant contains more than one such moiety, said moieties have up to two fluorinated or unfluorinated methyl branches, which surfactant is present in a molar ratio to said substrate of from about 0.01:1 to about 10:1.

8. The element of claim 7 wherein said fluorinated surfactant is selected from the group consisting of a perfluoroalkyl quaternary ammonium salt and a perfluoroalkyl betaine.

9. The element of claim 7 wherein said fluorinated surfactant is located in said spreading layer.

10. The element of claim 7 wherein said particles comprise an addition polymer formed from one or more of the following ethylenically unsaturated polymerizable monomers:
  (a) up to 100 weight percent of an amino-substituent-free vinyl carbocyclic aromatic,
  (b) up to about 25 weight percent of an acrylic acid ester,
  (c) up to 100 percent of a methacrylic acid ester,
  (d) up to about 30 weight percent of an ethylenically unsaturated carboxylic acid
  (e) up to about 75 weight percent of an ethylenically unsaturated nitrile,
  (f) up to about 20 weight percent of an amino-substituted vinyl carbocyclic aromatic,
  (g) up to about 20 weight percent of an ethylenically unsaturated crosslinkable monomer,
  (h) up to about 20 weight percent of a tertiary aminoalkyl acrylate or methacrylate,
  (i) up to 100 weight percent of an N-heterocyclic vinyl monomer, and
  (j) up to about 20 weight percent of an acrylamide or methacrylamide,
  and said adhesive comprises an addition polymer formed from ethylenically unsaturated polymerizable monomers selected from the following group:
  A. A blend containing from about 1 to about 35 weight percent of one or more amino-substituent-free vinyl carobcyclic aromatics and from about 65 to about 99 weight percent of one or more alkyl acrylates or methacrylates,
  B. a blend containing from about 20 to about 95 weight percent of one or more amino-substituent-free vinyl carbocyclic aromatics, acrylic or methacrylic acid esters and ethylenically unsaturated polymerizable crosslinkable monomers, and from about 5 to about 80 weight percent of one or more ethylenically unsaturated polymerizable monomers having an active hydrogen or salts thereof,
  C. a blend containing from about 15 to 100 weight percent of one or more ethylenically unsaturated monomers selected from the group consisting of 1-vinylimidazole, N-vinyl-2-pyrrolidone, vinylbenzyl alcohol, ethyl acrylate or an acrylamide or methacrylamide, and up to 85 weight percent of one or more ethylenically unsaturated polymerizable crosslinkable monomers, and
  D. a blend containing from about 80 to about 98 weight percent of one or more acrylic or methacrylic acid esters, and from about 2 to about 20 weight percent of one or more ethylenically unsaturated polymerizable monomers containing one or more anionic moieties.

11. The element of claim 7 wherein said substrate is pyruvic acid or a salt thereof, and said indicator material is nicotinamide adenine dinucleotide, reduced form.

12. A method for the determination of total lactate dehydrogenase (LDH) comprising the steps of:
  A. in the presence of a substrate for LDH, an indicator material which provides a detectable change in response to the reaction of LDH with said substrate, and a saturated or unsaturated fluorinated surfactant containing one or more fluorocarbon moieties each having from 4 to 16 carbon atoms and from 8 to 33 fluorine atoms, and each of said moieties having a ratio of fluorine atoms to carbon atoms of about 2:1,
  provided that when said fluorinated surfactant contains more than one fluorocarbon moiety, said moieties have up to two fluorinated or unfluorinated methyl branches,
  contacting an analytical element with a sample of a liquid suspected of containing LDH, said element comprising a support having thereon a porous spreading layer composed of a particulate structure comprising a plurality of particles being bonded to each other on surface areas of adjacent particles where the adjacent particles are in closest proximity to form a coherent, three dimensional lattice which is essentially non-swellable in an aqueous liquid, and
  B. determining total lactate dehydrogenase by detecting the rate of said detectable change.

13. A metod for the determination of total lactate dehydrogenase (LDH) comprising the steps of:
  A. in the presence of a substrate for LDH and an indicator material which provides a detectable change in response to the reaction of LDH with said substrate, contacting a dry analytical element with a sample of a liquid suspected of containing LDH, said element comprising a support having thereon
  a porous spreading layer composed of a particulate structure comprising a plurality of particles being bonded to each other on surface areas of said particles which are adjacent, where said adjacent particles form a coherent, three dimensional lattice which is essentially non-swellable in an aqueous liquid,
  said element further comprising a saturated or unsaturated fluorinated surfactant containing one or more fluorocarbon moieties each having from 4 to 16 carbon atoms and from 8 to 33 fluorine atoms, and each of said moieties having a ratio of fluorine atoms to carbon atoms of about 2:1, provided that when said surfactant contains more than one such moiety, said moieties have up to two fluorinated or unfluorinated methyl branches, and
  B. determining total lactate dehydrogenase by detecting the rate of said detectable change.

14. The method of claim 13 wherein said detectable change is a spectrophotometric change.

15. The method of claim 14 wherein said detectable change is a colorimetric change.

16. The method of claim 15 wherein the rate of disappearance of absorption is detected.

17. A method for the determination of total lactate dehydrogenase (LDH) comprising the steps of:
  A. contacting a dry multilayer analytical element with a sample of a liquid suspected of containing LDH to provide a detectable colorimetric change, said element comprising a support having thereon, in order from said support and in fluid contact, a registration layer comprising an indicator material which provides a detectable spectrophotometric change in response to the reaction of LDH with a substrate for LDH, and an isotropically porous spreading layer comprising said LDH substrate and composed of a particulate structure comprising:

(i) a plurality of heat-stable, organo-polymeric particles non-swellable in and impermeable to an aqueous liquid, and having a particle size of from about 1 to about 200 $\mu$m, and (ii) an adhesive, in an amount of up to about 10 weight percent of said particles, comprising an organic polymer different from that of said particles, substantially all of said adhesive being concentrated on surface areas of adjacent particles where said adjacent particles are in closest proximity, and bonding said particles into a coherent, three-dimensional lattice which is essentially non-swellable in said liquid, said element containing, in any of said layers, a saturated or unsaturated fluorinated surfactant containing one or more fluorocarbon moieties each having from 4 to 16 carbon atoms and from 8 to 33 fluorine atoms, and each of said moieties having a ratio of fluorine atoms to carbon atoms of about 2:1, provided that when said surfactant contains more than one such moiety, said moieties have up to two fluorinated or unfluorinated methyl groups, which surfactant is present in a molar ratio to said substrate of from about 0.01:1 to about 10:1, and B. determining total lactate dehydrogenase by detecting the rate of said colorimetric change.

18. The method of claim 17 wherein said liquid is human serum or whole blood.

19. The method of claim 17 wherein the rate of disappearance of absorption is detected.

* * * * *